US00PP11211P

United States Patent [19]

Kordes et al.

[11] Patent Number: Plant 11,211

[45] Date of Patent: Feb. 8, 2000

[54] ***PHYSOCARPUS OPULIFOLIUS* CV 'MONLO'**

[75] Inventors: Gunter Kordes, Bilsen; Hans Schadendorf, Ellerbek, both of Germany

[73] Assignee: Monrovia, Azusa, Calif.

[21] Appl. No.: 09/006,709

[22] Filed: Jan. 14, 1998

[51] Int. Cl.[7] ..... A01H 5/00

[52] U.S. Cl. ..... Plt./226

[58] Field of Search ..... Plt./226, 263

[56] References Cited

PUBLICATIONS

Huxley et al. ed., 1992, The New Royal Horticultural Society Dictionary of Gardening, The MacMillan Press, Ltd., London, pp. 566–567.

*Primary Examiner*—Howard J. Locker

[57] ABSTRACT

A new and distinct selection of Ninebark, *Physocarpus opulifolius*, which shall be referred to hereinafter as cultivar 'Monlo'. Cultivar 'Monlo' differs distinctively from other *Physocarpus opulifolius* plants by possessing a unique combination of an outstanding cold hardy shrub with intense foliage color throughout the seasons peaking in summer to a maroon red and contrasting to the creamy-white flowers.

2 Drawing Sheets

BACKGROUND OF THE INVENTION

This invention relates to a new and distinct selection of *Physocarpus opulifolius*, a member of the Rosaceae family. We discovered the new selection, cultivar 'Monlo' as a seedling in June 1968 from a field of 120,000 other seedlings. The discovery was based on the red foliage this one particular seedling exhibited in this large field planting of all typically green foliaged plants in Ellerbek, Schleswig-Holstein, near Hamburg in Germany.

The new plant has been asexually reproduced by cuttings at Kordes Jungpflanzen, Muhlenweg 8, Bilsen in Germany and recently at Monrovia Nursery, 18331 East Foothill Boulevard, Azusa, Calif.

The discovery substantially differs by the unique characteristic of red foliage which sets the claimed plant apart from other *Physocarpus opulifolius* plants and cultivars which I am aware. Had the initial seedling not been successfully sown and discovered it may have been lost to mankind. It is unlikely the favorable attributes of this plant could be conveyed to progeny through sexual reproduction. However, through extensive asexual propagation by rooting cuttings of this plant it has been established that the novel, exceptional characteristics are stable and reliably passed on to clonal specimens.

SUMMARY OF THE INVENTION

To my knowledge, *Physocarpus opulifolius* cultivar 'Monlo' is the only red foliaged Ninebark. Ninebarks typically exhibit green foliage. There do exist some selections which have a yellow to yellow green foliage. My selection changes seasonally and after winter dormancy the first foliage to emerge in spring is dark red, summer foliage matures to a maroon dark red and autumn foliage changes to a dark brown red. This spectacular red seasonal foliage color of my selection adds an attribute to a widely used landscape pant.

Ninebarks are grown as background foliage shrubs. They are remarkably free from pest and diseases and their adaptation to different soil types and shade or sun and cold temperatures make this a versatile landscape addition. Pruning and shearing are easily tolerated. Plants which are not sheared exhibit a lovely natural growth habit. Winter is the dormant season with branches free from foliage exhibiting a exfoliating bark.

Typically white to pinkish clusters of flowers appear in late spring to early summer on *Physocarpus opulifolius*. My cultivar 'Monlo' has a cream white flower color which contrasts beautifully with the red foliage.

BRIEF DESCRIPTION OF DRAWINGS

The illustration of the discovery shows the maroon reddish summer foliage. Displayed in a corner inset is an inflorescence in full bloom contrasting with the maroon reddish foliage.

The other illustration displays the overall growth habit.

BOTANICAL DESCRIPTION

Below is a detailed description of *Physocarpus opulifolius* cv. 'Monlo'. The color terminology is from The Royal Horticultural Colour Charts. Plant size and description are based on plants growing in Bilsen, Germany and Azusa, Calif.

Overall size: Eight years old plant not pruned or sheared is 3 meters in height and 2.5 meters in width. Ultimate size estimated to be 4 meters in height and width which is characteristic of the species.

Overall habit: Deciduous shrub erect slightly spreading, stiff branches.

Overall cold hardiness: Outstandingly cold hardy to −30° C.

Foliage (data recorded October 1997 from plants grown in California unless other wise noted):

*Length.*—7.4 cm to 9 cm, occasionally to 13 cm.

*Width.*—5 cm to 7 cm.

*Shape.*—Generally 3 lobed, to 5 lobed.

*Margin.*—Serrate to dentate.

*Base.*—Slightly cordate on mature foliage, cuneate on foliage below inflorescence.

*Apex.*—Acute.

*Texture.*—Glabrous.

*Color.*—Upper mature and juvenile: Green group 139A Mixed with Red Purple Group 59A. In Germany in spring and summer Greyed Purple Group 187A and 187B.

*Midrib.*—Yellow-Green Group 144A. Lower mature and juvenile: Green Group 178B mixed with Red- Purple Group 59C. Midrib: juvenile, Red-Purple Group 59C. Midrib: mature Yellow Green Group 144B.

*Petiole*.—Color: Red-Purple Group 59A on juvenile. Length: 4.0 cm to 4.5 cm.

*Stipules*.—Color: Green Group 143A and Yellow Green Group 144B. Length: to 9 mm, 2 parted.

Bark:

*Juvenile*.—Color: Red-Purple Group 59A. Texture: Distinct 5 ridges on stems.

*Mature*.—Color: Greyed-Purple Group 187A. Texture: Distinct 2 ridges on stems, exfoliating.

Flowers:

*Arrangement*.—Corymb.

*Corymb*.—Diameter approximately 5 cm, composed of 30–56 flowers.

*Individual petals*.—4 mm wide, 5 mm long 5 per flower.

*Color*.—Creamy-White, Yellow-White Group 158D to White Group 155C with Yellow center of stamens.

*Lastingness*.—of corymb 14 to 20 days. of individual flowers 2–3 days.

*Bloom season*.—June and July in Germany.

*Flower buds*.—Prior to anthesis Red-Purple Group 65D.

*Pedicels*.—1.7 cm to 1.3 cm long.

*Sepals*.—5 in number. Color at anthesis: White Group 155A. Color after anthesis: Purple Group 75A and Purple 75B, later sepals brown and dry.

*Stamens*.—Numerous.

*Style*.—4.

*Fragrance*.—Slight sweet odor.

*Pest and disease resistance*.—Typical of species.

We claim:

1. A new and distinct selection of *Physocarpus opulifolius* plant as substantially shown and described herein, that is characterized particularly as novel by the unique combination of an outstanding cold hardy shrub with intense foliage color throughout the seasons peaking in summer to a maroon red and contrasting to the creamy white flowers.

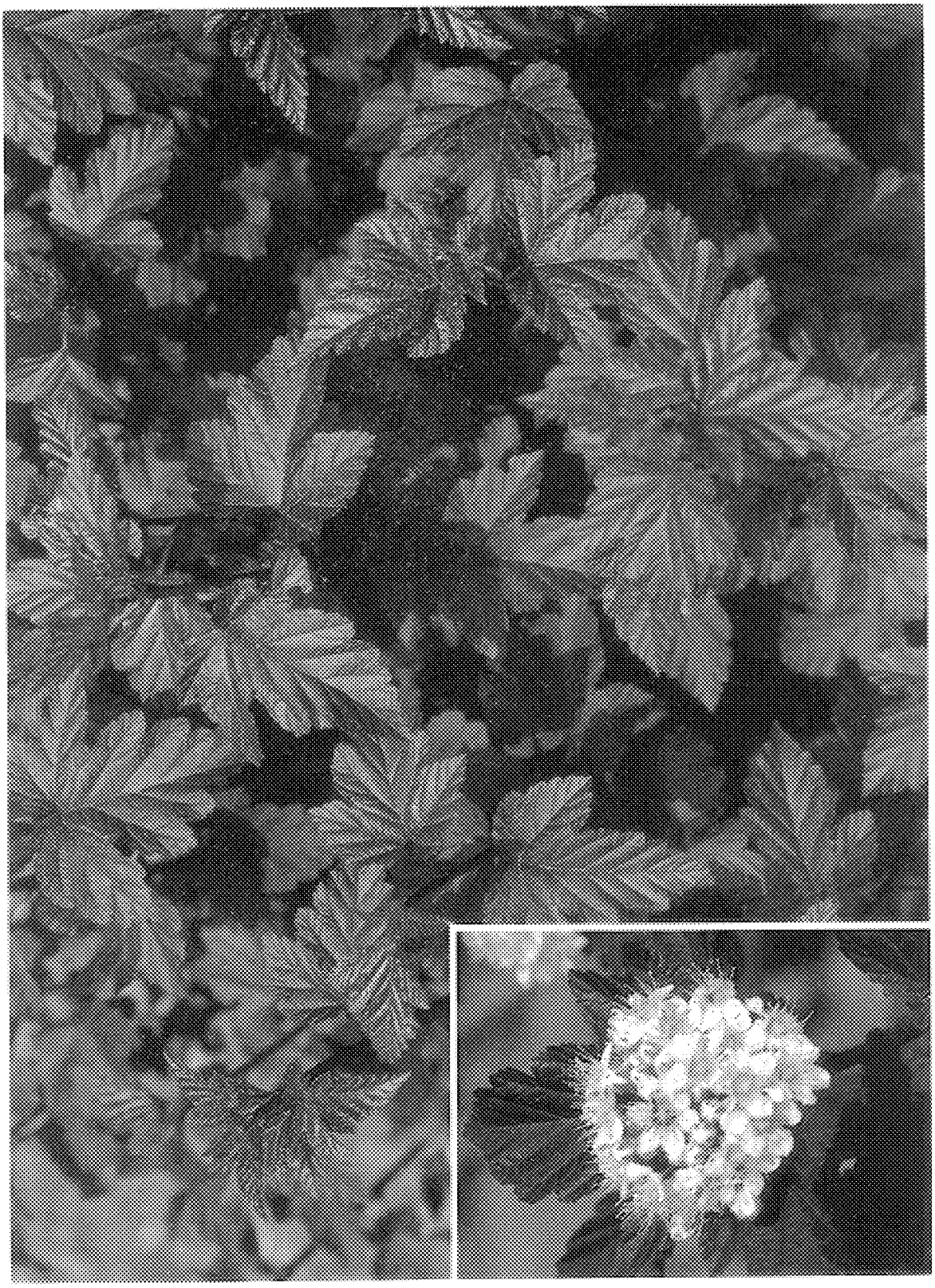

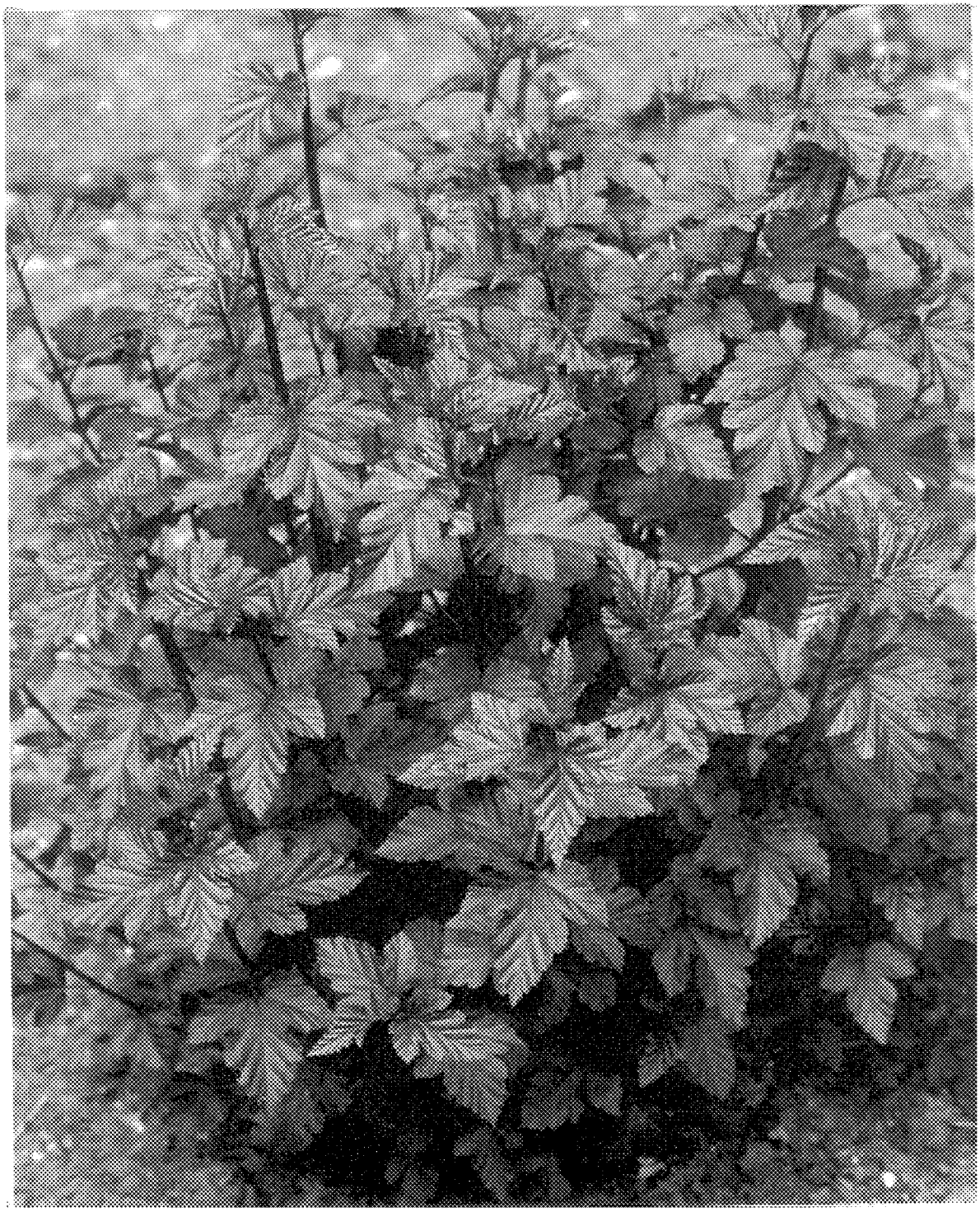

* * * * *